United States Patent [19]

Rieger et al.

[11] Patent Number: 5,753,144
[45] Date of Patent: May 19, 1998

[54] STABLE HOMOGENEOUS FORMULATIONS OF OXIDATON- SENSITIVE ORGANOMETALLIC COMPOUNDS IN PARAFFINS AND PROCESS FOR THEIR PREPARATION

[75] Inventors: Rainer Rieger, Lünen; Hans-Günter Volland, Unna; Wolfram Uzick, Schwerte, all of Germany

[73] Assignee: Witco GmbH, Bergkamen, Germany

[21] Appl. No.: 804,474

[22] Filed: Feb. 21, 1997

[30] Foreign Application Priority Data

Mar. 19, 1996 [EP] European Pat. Off. .............. 96104249

[51] Int. Cl.[6] .................................................. C09K 15/32
[52] U.S. Cl. .................. 252/400.41; 252/400.52; 252/400.61
[58] Field of Search .................. 252/400.52, 400.41, 252/400.61

[56] References Cited

U.S. PATENT DOCUMENTS 5,403,942  4/1995  Becker et al. .................. 502/152
5,534,474  7/1996  Becker et al. .................. 556/175

FOREIGN PATENT DOCUMENTS

| 622 826 | 2/1991 | Australia . |
| 2053199 | 4/1922 | Canada . |
| 0 344 887 A3 | 12/1989 | European Pat. Off. . |
| 0 420 436 A1 | 9/1990 | European Pat. Off. . |
| 0 416 815 A2 | 3/1991 | European Pat. Off. . |
| 0 520 732 A1 | 12/1992 | European Pat. Off. . |
| 0 530 908 A1 | 3/1993 | European Pat. Off. . |

OTHER PUBLICATIONS

Kirk–Othmer, Encyclopedia of Chemical Technology, vol. 24, Third Edition, pp. 471–478 (1985).

*Primary Examiner*—Mukund J. Shah
*Assistant Examiner*—Bruck Kifle
*Attorney, Agent, or Firm*—Scully, Scott, Murphy & Presser

[57] ABSTRACT

Disclosed are homogeneous formulations consisting essentially of one or more oxidation-sensitive organometallic compounds in a hydrocarbon, such as paraffins having a boiling point of at least 150° C. and a viscosity of at least 1 Pa.s at 25° C. Also disclosed is a process for the preparation of these formulations.

12 Claims, No Drawings

STABLE HOMOGENEOUS FORMULATIONS OF OXIDATON- SENSITIVE ORGANOMETALLIC COMPOUNDS IN PARAFFINS AND PROCESS FOR THEIR PREPARATION

BACKGROUND OF THE INVENTION

Organometallic compounds, such as magnesium alkyl, boron alkyl, zinc alkyl compounds, or aluminum alkyls and partial hydrolysis products thereof, such as aluminoxanes, are important components of modern chemical processes.

The industrially used metal alkyls are highly reactive compounds. Their high reactivity plays an important role in industrial applications, as a result of which more stringent safety precautions must also be taken during handling.

When such metal alkyls come into contact with air, very violent oxidation and decomposition reactions take place immediately. For aluminum alkyls with 1 to 6 C atoms per alkyl group, for example, the generated heat of reaction is so high that, as a rule, spontaneous ignition takes place.

The property of spontaneous ignition or pyrophoricity of metal alkyls and their solutions make special and time- and cost-consuming safety precautions necessary during handling, storage and transportation.

Due to the high reactivity of these compounds, mainly inert aromatic or saturated aliphatic hydrocarbons are taken into consideration as solvents. It should be recalled that the flammability of relatively low-boiling hydrocarbons is further increased by dissolved metal alkyls since the heat of oxidation which is generated during discharge increases the evaporation of the solvent. Even highly diluted metal alkyl solutions must be handled in a protective atmosphere to prevent oxidation, thus decreasing the quality of the product.

Metal alkyls react even more violently with water than they do with air. In the case of very low metal alkyls, for example, a large quantity of readily ignitable gases is abruptly released in this extremely vehement and highly exothermal reaction. In addition, as the temperature increases, decomposition reactions take place.

One drawback is that in aliphatic saturated hydrocarbons, some of the industrially relevant organometallic compounds are often soluble only to limited extent. For this reason, but also to avoid the pyrophoricity and spontaneous ignition, often highly diluted solutions cannot be avoided, which entails corresponding disadvantages during transport and storage. Especially methyl aluminoxane, however, is readily soluble only in aromatic hydrocarbons, such as benzene and toluene. In higher concentrations, it also has only a limited storage life since it tends to form gel-like precipitates. The gelled solutions are homogeneous and can be handled only with great difficulty.

Furthermore, aromatic solvents as such are controversial due to toxicological considerations, especially in association with applications of catalyst systems for the production of polyolefins that are used in the food industry and in medicine.

Therefore, the problem to be solved by this invention was to overcome these drawbacks and to develop homogeneous and highly concentrated formulations which are storage-stable over long periods of time, especially for aluminum alkyls as well as chemically related metal alkyls which formulations, even in high concentrations, are neither spontaneously ignitable nor pyrophoric.

BRIEF SUMMARY OF THE INVENTION

This problem is solved by dissolving the metal alkyls in high-boiling hydrocarbons (paraffins), which, at room temperature, have an oily or waxlike consistency, by means of suitable mixing devices, and by suspending or dispersing them (hereinafter referred to as formulations).

There are principally different methods by means of which formulations according to this invention can be prepared following the process according to this invention, e.g.:

M1) Preparation of the organometallic compounds in a nonaromatic dispersing/suspending agent or solvent M2) Dissolution, suspension, or dispersion of isolated organometallic compounds M3) Mixing of nonaromatic solvents or dispersing agents with solutions of the organometallic compounds and subsequent separation of the solvent by means of distillation, thus obtaining the solutions, suspensions, or dispersions according to this invention.

To prepare the formulations, the organometallic compounds can be used in pure form as well as on a suitable support material. If the organometallic compounds are used in pure form the support material can be added to the processing possibilities M1–M3 at any time.

DETAILED DESCRIPTION OF THE INVENTION

Specific examples of the processing possibilities M1–M3 follow:

As to M1): An aluminoxane in a nonaromatic high-boiling solvent is prepared in a jet loop reactor following European Patent Application EP-A-0,623,624. The high shearing forces that are generated ensure an excellent reaction of the aluminum alkyl with water, without leading to a total hydrolysis to form inorganic $Al(OH)_3$. In contrast to the patent application mentioned above, the process is carried out at higher temperatures since the paraffins used have a considerably higher viscosity and the formulations obtained further contribute to an increase in the viscosity.

As to M2): The formulation of aluminoxanes that are insoluble in the liquid and waxlike paraffins used is carried out utilizing high shear forces to obtain the finest possible homogeneous distribution of the insoluble particles. The process can be carried out both at increased and at decreased temperatures. The consistency of the formulation obtained depends on the paraffins used and on the temperature that prevails during mixing.

As to M3): The nonaromatic formulation medium is mixed with a solution of aluminoxane, and subsequently, the solvent of the aluminoxane is removed in vacuo or at an increased temperature while subjecting it to considerable agitation, which leads to a remaining solution/suspension/dispersion with properties that are comparable to those of the products prepared by means of the processes above.

Surprisingly, it was discovered that even at high aluminoxane concentrations, the aluminoxane formulations thus prepared are no longer spontaneously ignitable or pyrophoric. Even at increased temperatures, they are even comparatively resistant to water.

Thus, on direct contact with water, they react while liberating only moderate quantities of methane gas, even if the formulation contains more than 30 wt. % of aluminum corresponding to a much higher content of organometallic compounds, in the case of methyl aluminoxane of approximately 65–70 wt. %.

Depending on the formulation medium used, it is possible to obtain homogeneous viscous but still pumpable liquids that are stable at room temperature or homogeneous waxlike to free-flowing products.

One subject matter of this invention therefore concerns a process for the production of homogeneous mixtures which consist essentially of one or more oxidation-sensitive organometallic compounds and formulation media, in which A) the organometallic compound is prepared according to substantially known methods directly in the hydrocarbon used or B) the isolated organometallic compound is dissolved, suspended or dispersed in the hydrocarbon used, or C) the solution of the organometallic compound, which was prepared according to known methods, in low-boiling solvent is introduced in a first step into the paraffin used according to this invention and the low-boiling solvent is removed in a second step, optionally by also using D) conventional auxiliary agents and admixtures, additives, and inorganic or organic support materials.

Another subject matter of this invention concerns the formulation that is prepared using the process according to this invention.

Other subject matter of this invention are defined by the claims.

The formulation media useful according to this invention include all natural or synthetic commercially available long-chain, optionally branched liquid or solid hydrocarbons with boiling points above 150° C., preferably above 200° C., and viscosities of at least 1 Pa.s at 250°.

These compounds include the product groups of the so-called white mineral oils, e.g. Witco White Mineral Oil Parol® (trademark of Witco Polymers + Resins B.V., Netherlands), Vaseline, and paraffinic waxes, e.g., Terhell® (firm of Schumann).

Waxes used according to this invention are described, for example, in Kirk-Othmer, Encyclopedia of Chemical Technology, Interscience Publishers, John Wiley & Sons, New York City, 1984, 3rd edition, Vol. 24, pages 471–478.

The hydrocarbon used does not depend on the organometallic compound but is determined mainly by the practical requirements of future applications.

The organometallic compounds can be used in considerably higher concentrations than in prior art. The lower concentration range of approximately 0.01–10 wt. %, relative to the formulation, is not critical. According to this invention, the ranges to be preferred are higher than approximately 10–20 wt. %, preferably between 25 and 80 wt. %, relative to the formulation.

The oxidation-sensitive organometallic compounds used according to this invention are those on the basis of the elements of Groups IIA, IIIA, IVA, IVB, and IIB of the Periodic Table of the Elements, preferably aluminum-organic, boron-organic, zinc-organic, or magnesium-organic substances alone or in mixtures or as complex salts, such as $R^1R^2R^3Al$, $R^1R^2R^3B$, $R^1R^2Mg$, $R^1R^2Zn$, in which $R^1$, $R^2$, and $R^3$ are independent of each other hydrogen, an alkyl or alkoxy group containing preferably up to 12 carbon atoms, or halogen or hetero atoms, e.g., tributyl aluminum, triisobutyl aluminum, trihexyl aluminum, trioctyl aluminum, diethyl aluminum chloride, ethyl aluminum sesquichloride, ethyl aluminum dichloride, diisobutyl aluminum chloride, isobutyl aluminum dichloride, diethyl aluminum iodide, diisobutyl aluminum hydride, diethyl aluminum ethoxide, isoprenyl aluminum, dimethyl aluminum chloride, sodium butyl ethyl dihydridoaluminate, methyl aluminoxane, ethyl aluminoxane, tetraethyl aluminoxane, methyl aluminum sesquichloride, tetraisobutyl dialuminoxane, trimethyl aluminum and/or triethyl aluminum, preferably in mixtures with a minimum of one of the compounds mentioned, and as complex salt mixtures (e.g., EURELYTH® 5002, trademark of Witco GmbH, Germany), diethyl aluminum hydride, hexaisobutyl tetraaluminoxane, diethyl(dimethyl ethylsilanolato)aluminum, diethyl(ethylmethylsilanolato) aluminum, diisobutyl(methylsilanato)aluminum, tridodecyl aluminum, tripropyl aluminum, dipropyl aluminum chloride, dibutyl magnesium, butyl ethyl magnesium, butyl octyl magnesium, butyl octyl magnesium ethoxide, ethyl aluminum propoxychloride, triethylboron, dimethylzinc, diethylzinc, tris[pentafluorophenyl]borane and its salts, and metallocene compounds, such as are described in the European Patent Applications EP-A-0,480,390, EP-A-0,413,326, EP-A-0,530,908, EP-A-0,344,887, EP-A-0,420,436, EP-A-0,416,815, and EP-A-0,520,732.

Inorganic supporting materials useful according to this invention include porous oxides of one or more of the elements of Groups IIA, IIIA, or IVA or the Periodic Table of the Elements, such as $ZrO_2$, $TiO_2$, $B_2O_3$, CaO, ZnO, BaO, zeolites and preferably $Al_2O_3$ and MgO and especially $SiO_2$ (German Patent DE 4,409,249).

Organic supporting materials useful according to this invention include, for example, porous, partially polymeric compounds such as polyethylene, polypropylene, polystyrene, and sugar derivatives (starch, amylose, cyclodextrines).

EXAMPLES

Example 1

In a nitrogen atmosphere, 230 g of a 30% toluenic methyl aluminoxane (MAO) solution and 31 g of paraffin (Terhell® 5605, trademark of the firm of Schümann) were placed under a nitrogen atmosphere in a 500 mL flask with a high shear stirrer.

After heating to approximately 50° C., a homogeneous solution was obtained. Subsequently, the toluene was distilled off in vacuo at a bath temperature of up to 75° C. and a vacuum up to 0.1 mbar. This was followed by cooling, after which the solidified product was removed from the wall of the flask. After external cooling with dry ice, it was possible to disintegrate the solid into a fine-particle solid.

The powder which contained approximately 66% of MAO (corresponding to 30% of aluminum) was not pyrophoric or spontaneously ignitable.

Example 2

In a protective nitrogen gas atmosphere, 52.4 g of methylaluminoxane supported on silica (SYLOPOL® 2104, trademark of the firm of Grace) with an aluminum content of 23.8% were placed into a container and 3.14 g of EURECEN® 5036 (1,2-ethylene-bis(1-indenyl)zirconium dichloride were added. To this mixture of solids, 111.1 g of White Mineral Oil Witco parol® were added and stirred for 2 hours. A viscous curry-colored suspension was obtained. The resulting formulation had an aluminum content of 7.5%, corresponding to a content of organometallic compounds of 33%.

The formulation was neither pyrophoric nor spontaneously ignitable.

Example 3

In a three-neck flask, 56.8 g of $MAO/SiO_2$ (Al content 23.8%) were stirred for half an hour in an $N_2$ atmosphere with 40.1 g of Witco White Mineral Oil Parol®. The product obtained was a still free-flowing and powderlike product with an Al content of 13.95% and a solids content (MAO/SiO$_2$) of 58.6%. Again, this formulation was no longer pyrophoric. When it came into contact with water, considerable gas was generated and partial charring set in; however, ignition was not observed.

Example 4

In a three-neck flask, 26.3 g of MAO solid (Al content 39.2%) were stirred for one hour in an N$_2$ atmosphere with 7.3 g Witco White Mineral Oil Parol® by means of a high shear stirrer. A nonpyrophoric highly viscous formulation with an Al content of 30.1% and a trimethyl aluminum (TMA) content, corresponding to 3.6% of Al, was obtained.

This corresponded to an MAO content of 57% or a solids content of 78%. Even on direct contact with water, this formulation reacted only by generating methane; ignition did not take place at any time.

Example 5

In a three-neck flask with a thermometer, nitrogen gassing, and distillation bridge and a magnetically controlled high shear stirrer, 402 g of MAO solution (30% in toluene; 13.2% of Al, 3.19% of Al in the form of TMA (mean molecular weight: 1000 g/mol)) were mixed with 219 g of White Mineral Oil Parol®. At a maximum temperature of 32° C. and while stirring vigorously, the toluene was stilled off over a period of 6 hours and at 0.1 bar. 338 g of a viscous, free-flowing suspension/dispersion with an Al content of 13.4% and TMA content of 1.5 in the form of Al, the hydrolysis gas determination of which yielded 174 NmL/g, were obtain.

The Al content corresponded to an MAO content of approximately 26%.

The formation was neither pyrophoric nor spontaneously ignitable.

Example 6

In a 500 mL Schlenck tube (a high vessel was required to ensure that the mixture, which tends to form large quantities of bubbles during the vacuum generation, remained in a stirrable state) with nitrogen gassing, a distillation bridge, and a magnetically controlled high shear stirrer, 402 g of MAO solution (30% in toluene; 13.2% of Al, 3.19% of Al in the form of TMA (mean molecular weight: 1000 g/mole)) were mixed with 84 g of White Petroleum Jelly Snow Whites MD® (commercial product of the firm of Witco Polymers+Resins B.V., Netherlands). At 55° C.–60° C. and while stirring vigorously, the mixture was homogeneous, and at 650° C., the toluene was distilled off over a period of 6 hours and at 0.1 bar.

122 g of a colorless waxlike substance were obtained, which was free-flowing beginning at a temperature of approximately 60° C. The Al content was 12.0%, the TMA content was 1.5. The hydrolysis gas volume was 145 NmL/g. This corresponded to an MAO content of 22.6%.

The formulation was neither pyrophoric nor spontaneously ignitable.

Example 7

In a round bottom flask with a high shear stirrer, 33.5 g of methyl aluminoxane (solid) and 16.8 g of paraffin (Terhell® 5605, trademark of the firm of Schumann) were heated in a nitrogen atmosphere. At a bath temperature of 65°–70° C., an opaque melt was obtained. The melt was allowed to solidify while stirring continued and was subsequently removed from the wall of the flask. After external cooling with dry ice, it was possible to disintegrate the solid into a fine-particle solid.

The powder which contained approximately 66% of MAO (corresponding to 30% of aluminum) was neither pyrophoric nor spontaneously ignitable.

Example 8

In a 500-mL Schlenck tube (a high vessel was required to ensure that the mixture, which tends to form large quantities of bubbles during the vacuum generation, remained in a stirrable state) with nitrogen gassing, a distillation bridge, and magnetically controlled high shear stirrer, 221 g of BOMAG-A® (trademark of Witco GmbH) (20% in heptane, corresponding to 2.89% of Mg) were mixed with 102 g of White Mineral Oil Parol®. While stirring vigorously, the heptane was distilled off over a period of 4.5 hours and at 0.1 mbar and a temperature of 40° C.

A viscous liquid with an overall Mg content of 4.25% was obtained; this corresponded to a BOMAG-A® content of approximately 29.1%.

The formulation was neither pyrophoric nor spontaneously ignitable.

What is claimed is:

1. A process for the production of a homogeneous mixture consisting essentially of one or more oxidation-sensitive organometallic compounds comprising an element from Groups IIA, IIIA, IVA, IVB or IIB of the Periodic Table of Elements and a hydrocarbon selected from the group consisting of white mineral oils, petrolatum and paraffinic waxes comprising A) preparing the organometallic compound directly in the hydrocarbon, or B) preparing and isolating the organometallic compound separately and then suspending or dispersing it in the hydrocarbon, or C) introducing a solution of the organometallic compound in a low-boiling solvent in a first step into the hydrocarbon and removing the low-boiling solvent in a second step, D) wherein the homogeneous mixture also optionally contains one or more inorganic or organic support materials for supporting said organometallic compounds.

2. The process as claimed in claim 1, wherein the organometallic compound is an aluminum-organic compound.

3. The process as claimed in claim 1, wherein the organometallic compound is a magnesium-organic compound.

4. The process as claimed in claim 1, wherein the organometallic compound is a boron-organic compound.

5. The process as claimed in claim 1, wherein the organometallic compound is a zinc-organic compound.

6. The process as claimed in claim 1, wherein the organometallic compound is an aluminoxane.

7. The process as claimed in claim 1, wherein the organometallic compound is methyl aluminoxane.

8. The process as claimed in claim 1, wherein the organometallic compound is a halogen- or oxygen-substituted aluminum-organic compound.

9. The process as claimed in claim 1 wherein the hydrocarbon has a boiling point above 150° C. and a viscosity of at least 1 Pa.s at 25° C.

10. The process as claimed in any one of claims 1 through 9, wherein relative to the overall mixture, the organometallic compound concentration is 0.01 wt. % to 80 wt. %.

11. A homogeneous mixture prepared according to the process as claimed in claim 1.

12. A homogeneous mixture consisting essentially of one or more oxidation-sensitive organometallic compounds comprising an element from Groups IIA, IIIA, IVA, IVB or IIB of the Periodic Table of Elements and a hydrocarbon selected from the group consisting of white mineral oils, petrolatum and paraffinic waxes, wherein said hydrocarbon has a boiling point above 150° C. and a viscosity of at least 1 Pa.s at 25° C.

* * * * *

UNITED STATES PATENT AND TRADEMARK OFFICE
CERTIFICATE OF CORRECTION

PATENT NO. : 5,753,144
DATED : May 19, 1998
INVENTOR(S) : Rainer Rieger et al.

It is certified that error appears in the above-identified patent and that said Letters Patent is hereby corrected as shown below:

Title page, Item [54] and Column 1, line 2,
Title, "OXIDATON" should read -- OXIDATION --

Column 3,
Line 27, "250º" should read -- 25º --

Column 5,
Line 51, "650º C" should read -- 65º C --

Signed and Sealed this

Eleventh Day of May, 2004

JON W. DUDAS
*Acting Director of the United States Patent and Trademark Office*